(12) United States Patent
Müller et al.

(10) Patent No.: US 7,858,337 B2
(45) Date of Patent: Dec. 28, 2010

(54) PROCESS FOR THE MANUFACTURE OF A COMPOSITE MATERIAL

(75) Inventors: Achim Müller, Grossostheim (DE); Monika Knuth, Aschaffenburg (DE); Katharina Schmid, Aschaffenburg (DE); Ralf Pasternack, Griesheim (DE); Jens Zotzel, Darmstadt (DE); Kai Oertel, Mainz (DE); Christine Reiff, geb. Schmitt, Lörrach (DE); Hans-Lothar Fuchsbauer, Mühltal (DE)

(73) Assignee: Novartis AG, Basel (CH)

( * ) Notice: Subject to any disclaimer, the term of this patent is extended or adjusted under 35 U.S.C. 154(b) by 78 days.

(21) Appl. No.: 12/074,329

(22) Filed: Mar. 3, 2008

(65) Prior Publication Data
US 2009/0029413 A1    Jan. 29, 2009

(30) Foreign Application Priority Data
Mar. 8, 2007    (EP)    ................... 07103810

(51) Int. Cl.
C07K 7/00    (2006.01)
C12P 1/00    (2006.01)
C12P 21/04    (2006.01)

(52) U.S. Cl. .................... 435/68.1; 435/41; 530/300; 530/329

(58) Field of Classification Search ................ 435/68.1, 435/41; 530/300, 329
See application file for complete search history.

(56) References Cited

U.S. PATENT DOCUMENTS

| 4,136,250 A * | 1/1979 | Mueller et al. ............... 528/29 |
| 2003/0175745 A1 | 9/2003 | Dean et al. ...................... 435/6 |
| 2004/0224080 A1 | 11/2004 | Epstein et al. ............... 427/2.1 |
| 2006/0134166 A1 | 6/2006 | Luthra et al. ............... 424/422 |

FOREIGN PATENT DOCUMENTS

| WO | WO 00/18794 | 4/2000 |
| WO | WO 01/56627 A1 | 8/2001 |
| WO | WO 2004/050132 A2 | 6/2004 |

OTHER PUBLICATIONS

PCT International Search Report, (Sep. 2008).
PCT Written Opinion of the International Searching Authority, (Sep. 2008).
European Search Report, (Sep. 2007).
Examiners Communication.

* cited by examiner

Primary Examiner—Chih-Min Kam
(74) Attorney, Agent, or Firm—Jian Zhou

(57) ABSTRACT

The invention relates to a process for the manufacture of a composite materials comprising the steps of (a) providing a hydrophobic organic bulk material, and (b) applying a hydrophilic surface coating on the hydrophobic organic bulk material by first non-covalently attaching to the surface of the bulk material a water-soluble peptide comprising a hydrophobic moiety; and then chemically or enzymatically crosslinking the water-soluble peptide. The composite materials manufactured according to the process of the invention have desirable characteristics regarding adherence to the substrate, durability, hydrophilicity, wettability, biocompatibility and permeability and are thus particularly useful as ophthalmic devices.

14 Claims, No Drawings

PROCESS FOR THE MANUFACTURE OF A COMPOSITE MATERIAL

This application claims benefit under 35 USC §119 of European patent application No. EP 07103810.3 filed Mar. 8, 2007, the contents of which are incorporated herein by reference in its entirety.

INCORPORATION OF SEQUENCE LISTING

A paper copy of the Sequence Listing and a copy of the Sequence Listing on diskette, containing the file named 50700_US_NP_ST25.txt, which is 460 bytes in size (measured in MS-DOS) and created on Aug. 20, 2008, is herein incorporated by reference.

The present invention relates to a process for the manufacture of coated articles such as biomedical articles, especially contact lenses, which comprises at least partly coating said article with a crosslinkable hydrophilic peptide, and then chemically or enzymatically crosslinking said hydrophilic peptide.

A variety of different types of processes for preparing coatings on an "inert" hydrophobic substrate have been disclosed in the prior art. For example, WO-A-2004/050132 discloses to first of all provide a hydrophobic uncharged article surface with some bilayers composed of a polyacrylic acid and a polyallylamine hydrochloride and then to covalently attach an antibacterial peptide to the acidic component of the bilayers. However, the formation of the bilayers is time-consuming and their stability, in particular their long-term stability, is sometimes not totally satisfactory. This may in turn affect the wearer comfort of a biomedical article when worn in or on the human body, for example on the eye.

US-A-2006/0134166 discloses a method for making a non-crosslinked biodegradable copolymer coating on a surface of a medical device, wherein the copolymer is a polyamino acid which is derivatized to have a hydrophobic side chain.

US-A-2004/0224080 generally discloses an enzymatically crosslinked surface coating on a medical device, wherein lysine and glutamine are enzymatically crosslinked by use of transglutaminase.

US-A-2003/0175745 discloses that polypeptides can be used to coat solid surfaces of a biomedical device. It further discloses that peptides can be chemically crosslinked with glutaraldehyde.

In addition, known coating processes are in general batch processes, which are expensive to perform and which require extensive handling steps. Because of this, none of the existing processes is, for example, well suited for the integration into a fully automated high volume contact lens manufacturing process as described, for example, in EP-A-969956 or EP-A-1047542.

Accordingly, there is a need to provide new hydrophilic coatings on a hydrophobic biomedical article surface which on the one hand have an improved durability and cause an improved wearer comfort of the biomedical article, and which on the other hand may be manufactured in an easy way so as to be integrable in a mass manufacturing process.

Surprisingly, it has now been found, that hydrophobic articles may be rendered effectively hydrophilic on their surface by first non-covalently binding a peptide to the article surface and then subjecting said peptide to a crosslinking reaction.

The present invention therefore in one aspect relates to a process for the manufacture of a composite material comprising the steps of (a) providing a hydrophobic organic bulk material; and
(b) applying a hydrophilic surface coating on said bulk material by first non-covalently attaching to the surface of the bulk material a water-soluble peptide comprising a hydrophobic moiety; and then chemically or enzymatically crosslinking said water-soluble peptide.

The hydrophobic organic bulk material underlying the composite materials is preferably a material that is devoid of ionic groups such as cationic or anionic groups or has at least a relatively low concentration of ionic groups. Accordingly, the surface of the preferred bulk materials also has a low concentration of ionic groups or is even devoid of ionic groups such as carboxy, sulfo, amino and the like groups and thus may be substantially free of ionic charges.

Examples of suitable bulk materials are natural or synthetic organic polymers or modified biopolymers which are known in large number. Some examples of polymers are polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinyl acetate and polyacrylonitrile); or elastomers (silicones, polybutadiene and polyisoprene).

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates, polyalkyl (meth)acrylates, or fluorinated polyolefines, such as fluorinated ethylene or propylene, for example tetrafluoroethylene, preferably in combination with specific dioxols, such as perfluoro-2,2-dimethyl-1,3-dioxol. Mixtures of two or more of the above-mentioned materials are also possible.

Within the present invention polysiloxane hydrogels, perfluoroalkyl polyether hydrogels or mixtures thereof, in particular polysiloxane hydrogels, are the preferred hydrophobic organic bulk materials.

Examples of suitable polysiloxane hydrogels are, for example, those currently used for the manufacture of extended wear contact lenses, for example copolymers of (i) one or more hydrophilic monomers, for example selected from the group of hydroxyethylacrylate, hydroxyethylmethacrylate, acrylamide, N,N-dimethyl acrylamide, N-vinylpyrrolidone, acrylic or methacrylic acid, and (ii) a siloxane monomer and/or macromonomer, for example tris-trimethylsilyloxy-silyl-propyl methacrylate (TRIS), or a polysiloxane crosslinker, for example, as described in formula (2) below. Examples of suitable commercially available silicon hydrogels are Balafilcon A, Galyfilcon A, Lotrafilcon A, Lotrafilcon B or Senofilcon A.

Another group of preferred polysiloxane hydrogels are amphiphilic segmented copolymers comprising at least one hydrophobic siloxane or perfluoroalkyl polyether segment and at least one hydrophilic segment which are linked through a bond or a bridge member. Examples of said polysiloxane hydrogels are disclosed, for example, in PCT applications WO-A-96/31792 and WO-A-97/49740. A particularly preferred amphiphilic segmented copolymer comprises at least one hydrophobic segment selected from the group consisting of a polysiloxane, perfluoroalkyl polyether and a mixed polysiloxane/perfluoroalkyl polyether segment, and at least one hydrophilic segment selected from the group consisting of a polyoxazoline, poly(2-hydroxyethylacrylate), poly(2-hydroxyethylmethacrylate), polyacrylamide, poly(N,N-dimethylacrylamide), polyvinylpyrrolidone and a polyethyleneoxide segment.

Still another group of preferred polysiloxane hydrogels are those obtainable by crosslinking a crosslinkable or polymerizable prepolymer that is obtainable by (a) copolymerizing at least one hydrophilic monomer having one ethylenically unsaturated double bond and at least one siloxane crosslinker comprising two or more ethylenically unsaturated double bonds in the presence of a chain transfer agent having a functional group; and (b) reacting one or more functional groups of the resulting copolymer with an organic compound having an ethylenically unsaturated group. Polysiloxane hydrogels of this type are disclosed, for example in WO-A-01/71392.

A particularly preferred polysiloxane hydrogel is obtained by crosslinking a prepolymer which is obtainable by (a) copolymerizing a hydrophilic monomer of the formula

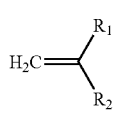

(1)

wherein $R_1$ is hydrogen or methyl, and $R_2$ is —COO—$(CH_2)_2$—OH, —$CONH_2$, —$CON(CH_3)_2$, or

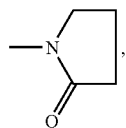

optionally in admixture with one or more further hydrophilic monomers; and a polysiloxane crosslinker corresponds to formula

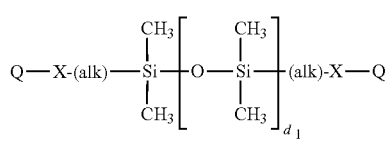

(2)

wherein $d_1$ is an integer from 10 to 500, preferably 10 to 300, more preferably 20 to 200 and in particular 25 to 150, (alk) is linear or branched $C_2$-$C_4$ alkylene or a radical —$(CH_2)_{1-3}$—O—$(CH_2)_{1-3}$—, X is —O— or —NH— and Q is a radical of the formula

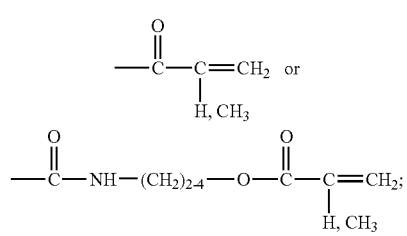

in the presence of a chain transfer agent having a functional group, in particular 2-mercaptoethanol or especially 2-aminoethane thiol (cysteamine); and (b) reacting the resulting copolymer with an organic compound having an ethylenically unsaturated group, for example with 2-isocyanatoethylmethacrylate (IEM), 2-vinyl-azlactone, 2-vinyl-4,4-dimethyl-azlactone, acryloyl or methacryloyl chloride, 2-hydroxyethylacrylate (HEA), 2-hydroxymethacrylate (HEMA), glycidylacrylate or glycidylmethacrylat, in particular with IEM or acryloyl chloride.

The water-soluble peptide being attached to the bulk material surface is, for example, a peptide of the formula

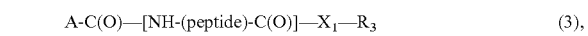

(3), wherein A-C(O) is a hydrophobic radical, for example a radical selected from the group consisting of the radical of a fatty acid, the radical of an aromatic carboxylic acid and the radical of an araliphatic carboxylic acid,

[NH-(peptide)-C(O)] is the radical of a polypeptide having an amino acid sequence comprising three or more amino acids, at least one of them being lysine (Lys) or glutamine (Gln), $X_1$-$R_3$ is either OH and part of the terminal peptide carboxy group, or $X_1$ is O or $NR_4$ wherein $R_4$ is hydrogen or $C_1$-$C_2$-alkyl, and $R_3$ is a hydrophilic group.

A-C(O) as the radical of a fatty acid is, for example, the radical of a long-chain aliphatic monocarboxylic acid, which contains, for example, from 6 to 25 carbon atoms and optionally comprises one or more carbon-carbon double bonds. Preferably, A-C(O) is the radical of a monocarboxylic acid of the formula $C_nH_{2n+1}COOH$, wherein n is a number from 7 to 20 and in particular from 8 to 18. Examples of preferred fatty acid radicals A-C(O) are the acyl radical of caprinic acid, laurinic acid, palmitinic acid or stearinic acid.

Examples of suitable aromatic acid radicals A-C(O) are the acyl radical of an optionally substituted benzoic acid or of a naphthoic acid.

Examples of a suitable radical of an araliphatic acid A-C(O) are the radical of an optionally substituted phenyl acetic or propionic acid or the radical of an 1- or 2-naphthyl acetic or propionic acid.

Optional substitutents of the benzoic, phenylacetic or phenylpropionic acid are, for example, $C_1$-$C_2$-alkyl or $C_1$-$C_2$-alkoxy.

The amino acid sequence (peptide) in general may be the radical of any water-soluble peptide which is chemically or enzymatically crosslinkable.

The amino acid sequence underlying the polypeptide radical [NH-(peptide)-C(O)] is preferably a sequence which may function as a substrate for the enzyme transglutaminase, that is it contains lysine and/or glutamine in form of a transglutaminase leader sequence which may be crosslinked enzymatically.

Examples of suitable peptides underlying the polypeptide radical [NH-(peptide)-C(O)] are a protein hydrolysate, for example a casein hydrolysate; a glutene peptide; a polylysine; or a copolymer of lysine and one or more other amino acids, for example, selected from the group consisting of alanine, phenylalanine, serin, tyrosine and tryptophane.

The molecular weight of the polypeptide underlying the radical [NH-(peptide)-C(O)] is in general not critical but preferably has a value $M_r$ of $\leq 12000$. A preferred molecular weight range of $M_r$ is from 400 to 10000, more preferably from 400 to 5000 and in particular from 500 to 1500.

One group of preferred polypeptides underlying the radical [NH-(peptide)-C(O)] are polylysines; the molecular weight of said polylysines is preferably within the above-given ranges including the preferences.

A further group of preferred polypeptides are statistical copolymers of lysine and one or more amino acids selected from the group consisting of alanine, phenylalanine, serin, tyrosine and tryptophane, wherein again the above given ranges and preferences for the molecular weight apply.

A further suitable lysine copolymer has a statistical composition consisting of: from zero to one, preferably one tyrosine (Tyr) residue; from 0 to 8, preferably from 1 to 5 and in particular from 2 to 4 alanine (Ala) residues; from 1 to 20, preferably from 2 to 10, and in particular from 2 to 5 lysine (Lys) residues; the total number of the amino acid residues in the lysine copolymer is from 3 to 20, preferably from 4 to 12 and in particular from 5 to 8.

Within this group of lysine copolymers, [NH-(peptide)-C(O)] is preferably the radical of a polypeptide having a statistical composition consisting of one tyrosine (Tyr) residue, 3 alanine (Ala) residues, and 3 lysine (Lys) residues and even more preferred the radical of a synthetic polypeptide of the SEQ ID NO 1:

Tyr-Ala-Lys-Ala-Lys-Lys-Ala wherein Tyr is linked to A, and Ala is linked to $R_3$.

A further group of preferred polypeptides underlying the radical [NH-(peptide)-C(O)] comprises a glutene peptide comprising glutamine units.

Still a further group of preferred polypeptides underlying the radical [NH-(peptide)-C(O)] comprises a casein hydrolysate comprising glutamine and lysine units.

$X_1$ in formula (3) is preferably O or NH, in particular NH.

$R_3$ as a hydrophilic group denotes, for example, hydrogen or a $C_1$-$C_6$-alkyl radical which is substituted once or several times by sulfo, sulfato, phosphato and/or carboxy. The terms sulfo, sulfato, phosphato and carboxy in general include the free acid as well as biomedically acceptable, in particular opthalmically acceptable, salts thereof, for example sodium, potassium, magnesium or ammonium salts. Preferably, $R_3$ as a hydrophilic group denotes a $C_1$-$C_4$-alkyl radical which is mono- or disubstituted by sulfo, sulfato and/or carboxy. More preferably, $R_3$ as a hydrophilic group is a $C_2$-$C_3$-alkyl radical which is monosubstituted by sulfo or carboxy. Most preferably, $R_3$ as hydrophilic group is 2-sulfoethyl.

In case $X_1$-$R_3$ is OH, formula (3) is meant to cover as well suitable salts of the terminal carboxy group, for example the sodium, potassium or an ammonium salt.

According to a preferred embodiment of the invention there is attached to the hydrophobic organic bulk material in step (b) a water-soluble peptide of the above-given formula (3), wherein A-C(O) is the radical of a monocarboxylic acid of the formula $C_nH_{2n+1}COOH$, wherein n is from 7 to 20; [NH-(peptide)-C(O)] is an amino acid sequence derived from a polypeptide having a molecular weight of from 400 to 10000 which is selected from the group consisting of a protein hydrolysate, a glutene peptide, a polylysine, or a copolymer of lysine and one or more other amino acids, $X_1$ is O or NH, and $R_3$ is hydrogen or $C_1$-$C_4$-alkyl which is mono- or disubstituted by sulfo, sulfato and/or carboxy.

According to an even more preferred embodiment of the invention there is attached to the hydrophobic organic bulk material in step (b) a water-soluble peptide of the above-given formula (3), wherein A-C(O) is the radical of a monocarboxylic acid of the formula $C_nH_{2+1}COOH$, wherein n is from 8 to 18; [NH-(peptide)-C(O)] is an amino acid sequence derived from a polypeptide having a molecular weight of from 500 to 1500, which is selected from the group consisting of a casein hydrolysate; a glutene peptide; a polylysine; a statistical copolymer of lysine and one or more amino acids selected from the group consisting of alanine, phenylalanine, serin, tyrosine and tryptophane; and a polypeptide of the formula Tyr-Ala-Lys-Ala-Lys-Lys-Ala     (4c), wherein Tyr is linked to A, and Ala is linked to $R_3$, $X_1$ is O or NH, and $R_3$ is hydrogen or $C_2$-$C_3$-alkyl which is monosubstituted by sulfo or carboxy.

The compounds of the formula (3) may be synthesized by methods known per se. For example, a peptide of the formula $H_2N$-(peptide)-C(O)OH     (3a), wherein (peptide) is as defined above is reacted in any order with a compound of formula

A-COOH     (5), wherein A is as defined before, and, if applicable, with a compound of the formula $R_3$—$X_1$H     (6), wherein $R_3$ and $X_1$ are as defined above.

The compounds of formulae (5) and (6) are known and in general commercially available. The peptides of formula (3a) can be obtained in part from commercial suppliers or can be synthesized according to any known suitable method. For example polylysines and statistical copolymers of lysine and another amino acid may be obtained by standard copolymerization reaction. Specific polylysine copolymers may be obtained by solid phase peptide synthesis as described, for example, in W. C. Chan and P. D. White, *Fmoc Solid Phase Peptide Synthesis, Practical Approach Series*, Oxford University Press. For example, the peptides underlying the sequences of formulae (4a), (4b) and (4c), i.e. SEQ ID NO 1, can be synthesized by reacting the underlying protected amino acids—protected, for example, with the fluorenylmethoxycarbonyl (Fmoc) radical—one after another immobilized at a polymeric carrier, for example a polystyrene resin comprising chlorotrityl anchors. Accordingly, a first protected amino acid, for example Fmoc- and Boc (tert.-butylcarbonyl)-protected lysine or Fmoc-protected alanine, is coupled to the polymeric carrier. After completion of the coupling—which may be checked with the Kaiser test—said amino acid is deprotected—typically with diluted trifluoroacetic acid or with piperidine—before the coupling of the second protected amino acid is initiated. Following the coupling and deprotection of the last amino acid, the resulting peptide is separated from the polymeric carrier in a manner known per se, for example with a solution of trifluoroacetic acid in dichloromethane.

The reactions of the compound of formula (3a) with the compounds of the formula (5) and (6) are known per se from textbooks of Organic Chemistry. In case the peptide of formula (3a) is prepared by solid phase peptide synthesis as described above, the coupling of the compound of the formula (5) to the peptide preferably can be added to the peptide synthesis. Accordingly, to the peptide—before being separated from the polymeric carrier—is coupled the compound of formula (5) in the same manner as an amino acid.

The water-soluble peptide having the hydrophobic moiety is non-covalently attached to the hydrophobic bulk material surface. Accordingly attachment takes places, for example, by physical absorption, physical incorporation into the polymer matrix of the bulk material, complex formation, heteropolar bonding and/or by ionic interactions.

The attachment of the peptide to the bulk material surface may be accomplished according to processes known per se. For example, the bulk material is immersed in a solution of the peptide, or one or more layers of the peptide are deposited on the bulk material surface, for example, by dipping, spraying, printing, spreading, pouring, rolling or spin coating, spraying or particularly dipping being preferred.

A suitable dip solution of the peptide in general comprises the respective peptide diluted in one or more different solvents. Suitable solvents are, for example, water or an aqueous solution comprising a water-miscible organic solvent, for example THF or a $C_1$-$C_4$-alkanol such as methanol, ethanol or isopropanol; the preferred solvent is water. The pH of the aqueous solution of the peptide is dependent of the specific polypeptide used. A suitable buffer, for example a phosphate buffer, may be added to the dip solution in order to maintain a constant pH value. The dip solution may contain additional ingredients, for example salts. The concentration of the dip solutions may vary within wide limits depending, for example, dependant on the particular peptide involved. However, it is generally preferred to formulate relatively dilute solutions of the peptide.

The immersion time for the bulk material in the solution of the peptide may vary depending on a number of factors. In general an immersion time of from about 30 seconds to about 30 minutes, preferably from 30 seconds to 15 minutes and in particular from 45 seconds to 5 minutes, has proven as valuable. The immersion of the bulk material in the peptide solution may take place at room temperature or at an elevated temperature; accordingly, temperatures of, for example, from 15 to 30° C. as well as elevated temperatures of, for example, from 35 to 85° C. are possible.

A preferred embodiment of the invention comprises swelling the hydrophobic organic bulk material in a water-miscible organic solvent, for example, in a $C_1$-$C_4$-alcohol such as for example ethanol or isopropanol or in THF, before treating it with the solution of the peptide. The swelling may take place at ambient temperature or preferably at an elevated temperature of, for example from 35 to 90° C. The swelling time is not critical; usually a time period of from 30 seconds to 5 minutes, and preferably from 45 seconds to 2 minutes is sufficient.

Following the deposition of the peptide the bulk material may be worked up in an usual manner, for example by simple rinsing.

The hydrophilic surface coating (b) of the composite material according to the process of the present invention may be finalized, for example, chemically, by initiating the crosslinking of the non-covalently bound peptide on the organic bulk material. To this end the organic bulk material comprising the peptide on its surface is treated with a suitable crosslinking agent, for example with formaldehyde, preferably with an aqueous formaldehyde solution, or with glutar aldehyde.

Preferably, the hydrophilic surface coating (b) of the composite material according to the process of the present invention is finalized by enzymatical crosslinking. For example, in case the hydrophobic organic bulk material has attached to its surface a peptide comprising both lysine and glutamine units, said peptide may be crosslinked by the addition of a transglutaminase. The enzyme transglutaminase initiates the formation of intrapeptide and interpeptide isopeptide bonds between the lysine amino groups and glutamine amido groups. The treatment of the bulk material with the peptide attached to it in an aqueous solution comprising, for example, bacterial transglutaminase may take place at ambient temperature or preferably at a slightly elevated temperature of, for example from 30 to 50° C. The treatment time is not critical; usually a time period of from 30 seconds to 10 minutes, and preferably from 45 seconds to 5 minutes is sufficient.

In case the hydrophobic organic bulk material has attached to its surface a peptide comprising lysine units only or glutamine units only, enzymatical crosslinking using a transglutaminase is only feasible in the presence of a further protein or protein hydrolysate comprising the complementary amino acid units.

A further preferred embodiment of the invention therefore comprises a process for the manufacture of a composite material comprising the steps of
(a) providing a hydrophobic organic bulk material, and
(b) applying a hydrophilic surface coating on said bulk material by first
(b1) attaching to the bulk material surface a peptide comprising a hydrophobic moiety, which functions as a substrate for the enzyme transglutaminase, preferably a compound of the above-given formula (3), wherein the above-given meanings and preferences apply for the variables contained therein; then
(b2) adding a protein or protein hydrolysate to the bulk material surface which likewise functions as a substrate for the enzyme transglutaminase; followed by
(b3) treating with an enzyme, in particular a transglutaminase.

For example, the peptide in step (b1) comprises one or more glutamine units and the protein or protein hydrolysate in step (b2) comprises one or more lysine units; or, in another embodiment of the invention, the peptide in step (b1) comprises one or more lysine units and the protein or protein hydrolysate in step (b2) comprises one or more glutamine units.

It is believed that the transglutaminase treatment in the above process fixes and/or crosslinks the protein or protein hydrolysate on the peptide-modified surface of the hydrophobic bulk material. Suitable proteins or protein hydrolysates in step (b2) above are, for example, casein or casein hydrolysates, gelatine hydrolysates, gluten hydrolysates or soy protein hydrolysates, in particular casein hydrolysates. The treatment of the peptide-modified bulk material according to step (b1) with the protein or protein hydrolysate preferably takes place in an aqueous solution at ambient temperature. It follows a treatment with the enzyme at ambient temperature or preferably at a slightly elevated temperature of, for example from 30 to 50° C. The treatment time is not critical; usually a time period of from 30 seconds to 10 minutes, and preferably from 45 seconds to 5 minutes is sufficient.

The composite material obtained by the process of the invention preferably is a biomedical device, e.g. an ophthalmic device, preferably a contact lens including both hard and particularly soft contact lenses, an intraocular lens or artificial cornea, comprising a composite material as described above including all the above given definitions and preferences. The composite materials are further useful, for example, as wound healing dressings, eye bandages, materials for the sustained release of an active compound such as a drug delivery patch, moldings that can be used in surgery, such as heart valves, vascular grafts, catheters, artificial organs, encapsulated biologic implants, e.g. pancreatic islets, materials for prostheses such as bone substitutes, or moldings for diagnostics, membranes or biomedical instruments or apparatus.

According to the process of the invention, biomedical articles, in particular ophthalmic articles, are obtained that have a variety of unexpected advantages over those of the prior art, which make those articles very suitable for practical purposes, e.g. as contact lens for extended wear. For example, they do have a high surface wettability and lubricity. This can be demonstrated, for example, by the finger tip test showing a very slippery article surface; or by visual inspection; or by suitable contact angle measurements. For example, sessile drop static contact angles of coated and non-coated lenses are determined with a DSA 10 drop shape analysis system from Krüss (Krüss GmbH, Hamburg, Germany). While uncoated silicon hydrogel contact lenses in general have a water contact angle of 90 to 100° or above, a treatment according to the process of the invention significantly reduces said value. Further tools for assessing the superior quality of the surface coatings obtainable according to the process of the invention are ATR-FTIR measurements or the Sudan Black dye absorption test as described below in the Examples section.

In addition, biomedical devices, e.g. ophthalmic devices such as contact lenses, comprising a composite material obtained by the process of the invention have a very pronounced biocompatibility combined with good mechanical properties. In addition, there are generally no adverse eye effects observed, while the adsorption of proteins or lipids is low, also the salt deposit formation is lower than with conventional contact lenses. Generally, there is low fouling, low microbial adhesion and low bioerosion while good mechanical properties can be for example found in a low friction coefficient and low abrasion properties. Moreover, the dimensional stability of the composite materials of the invention is excellent. In addition, the attachment of a hydrophilic surface coating at a given bulk material according to the invention does not affect its visual transparency.

In summary, the ophthalmic devices obtained by the process according to the invention, such as intraocular lenses and artificial cornea or particularly contact lenses, provide a combination of low spoilation with respect to cell debris, cosmetics, tear components, lipids, proteins, salts, dust or dirt, solvent vapors or chemicals, with a high comfort for the patient wearing such opthalmic devices in view of the soft hydrogel surface which for example provides a very good on-eye movement of the ophthalmic device.

In the examples, if not indicated otherwise, amounts are amounts by weight, temperatures are given in degrees Celsius. Wetting force on the solid is measured as the solid is immersed in or withdrawn from a liquid of known surface tension. The amino acid starting materials as well as the amino acid units in the peptides are always present in the naturally occurring L-form unless indicated otherwise.

EXAMPLES

Example 1

Preparation of a Synthetic Polypeptide (Tyr-Ala-Lys-Ala-Lys-Lys-Ala) of the SEQ ID NO 1

The above-mentioned peptide is synthesized at a polystyrene carrier comprising 2-chlorotrityl anchors using standard methods of Fmoc-solid phase peptide synthesis. Couplings are in general performed in o-(benzotriazol-1-yl)-N,N,N',N'-tetramethyl-uroniumhexafluorophosphate (TBTU)/1-hydroxy-1H-benzotriazol (HOBt), and the completeness of a coupling is proven by the Kaiser test. Washing steps are performed with N,N-dimethyl formamide (DMF).

Detailed Procedure:
(a) 6.25 g of a commercially available Ala-OH-2-chlorotrityl-polystyrene carrier are suspended in 50 ml of dichloromethane in a peptide synthesis reactor and kept for 30 minutes. The polymeric carrier is washed with DMF and afterwards suspended again in some DMF.

(b) Coupling of Fmoc-Lys(Boc)-OH: 4.69 g of Fmoc-Lys(Boc)-OH, 3.14 g of TBTU and 1.35 g of HOBt are dissolved in 20 ml of DMF. 3.4 ml of N-ethyl-diisopropyl amine(DIPEA) are added to this solution. The resulting mixture is briefly stirred and is then added to the suspension obtained according to step (a). The resulting mixture is maintained under nitrogen for about one hour. Afterwards, a sample is taken and checked by the Kaiser test. In case the Kaiser test is negative, the reaction solution is extracted from the reactor, and the polystyrene carrier is washed ten times with DMF.

(c) Cleavage of the Fmoc protective group: To the resulting polymeric carrier after washing are added 30 ml of a DMF/piperidine mixture (80/20) and the whole is kept for one hour while flushing with nitrogen. The carrier is then again washed ten times with DMF and is afterwards suspended in some DMF.

(d) Coupling of Fmoc-Lys(Boc)-OH: In order to add the second Lys(Boc) to the Lys(Boc)-Ala-2-chlorotrityl-polystyrene prepared according to step (c), steps (b) and (c) are repeated in an identical manner.

(e) Coupling of Fmoc-Ala-OH: 3.11 g of Fmoc-Ala-OH, 3.14 g of TBTU and 1.35 g of HOBt are dissolved in 20 ml DMF. 3.4 ml of DIPEA are added to the resulting solution. The resulting mixture is briefly stirred and is then added to the suspension obtained according to step (d). The resulting mixture is kept under nitrogen for about one hour. Afterwards, a sample is taken and checked by the Kaiser test. In case the Kaiser test is negative, the reaction solution is extracted from the reactor, and the polystyrene carrier is washed ten times with DMF. It follows the cleavage of the Fmoc protective group which is performed as described in step (c).

(f) Coupling of another Fmoc-Lys(Boc)-OH and Fmoc-Ala-OH: Both amino acids are coupled to the peptide obtained according to step (e) in identical manner as described in steps (d) and (e) above.

(g) Coupling of Fmoc-Tyr(tBu)-OH (tBu=tert.-butyl): 4.6 g of Fmoc-Tyr(tBu)-OH, 3.14 g of TBTU and 1.35 g of HOBt are dissolved in 20 ml of DMF and afterwards 3.4 ml of N-ethyl-diisopropyl amine(DIPEA) added to this solution. The resulting mixture is briefly stirred and is then added to the suspension obtained according to step (a). The resulting mixture is maintained under nitrogen for about one hour. Afterwards, a sample is taken and checked by the Kaiser test. In case the Kaiser test is negative, the reaction solution is extracted from the reactor, and the polystyrene carrier is washed with DMF.

(h) Cleavage of the Fmoc protective group: To the resulting polymeric carrier after washing are added 30 ml of a DMF/piperidine mixture (80/20) and the mixture is kept for one hour while flushing with nitrogen. The resin is then washed three times with isopropanol and n-hexane and is afterwards dried in high vacuum. Yield: 12 g of a polystyrene resin loaded with a synthetic peptide of the SEQ ID NO:1 in which Tyr residue is protected with t-Bu group and Lys residues are protected with Boc groups.

Example 2a

Coupling of a Hydrophobic Moiety to a Peptide Using Solid Phase Chemistry 2.4 g of the polystyrene carrier loaded with a synthetic peptide of the SEQ ID NO:1 in which Tyr residue is protected with t-Bu group and Lys residues are protected with Boc groups obtained according to Example 1 are suspended with dichloromethane in a peptide reactor and kept for 30 minutes. The polystyrene carrier is then washed with DMF and afterwards suspended again in some DMF. In a separate jar 641 mg palmitinic acid, 786 mg TBTU and 338 mg HOBt are dissolved in DMF. Following the addition of 850 µl DIPEA and thorough stirring this solution is added to the suspended polystyrene carrier and the whole is maintained under nitrogen flushing for about one hour. After the completeness of the conversion has been confirmed by a Kaiser test, the polymeric carrier is washed with DMF.

Example 2b

Coupling of a Hydrophobic Moiety to a Peptide Using Solid Phase Chemistry 1 g of the polystyrene carrier loaded with a synthetic peptide of the SEQ ID NO:1 in which Tyr residue is protected with t-Bu group and Lys residues are protected with Boc groups obtained according to Example 1 are suspended with dichloromethane in a peptide reactor and kept for 30 minutes. The polystyrene carrier is then washed with DMF and afterwards suspended again in some DMF. In a separate jar 148 mg caprinic acid, 271 mg TBTU and 116 mg HOBt are dissolved in DMF. Following the addition of 293 µl DIPEA and thorough stirring this solution is added to the suspended polystyrene carrier and the whole is flushed with nitrogen for about two hours. After the completeness of the conversion has been confirmed by a Kaiser test, the reaction mixture is filtrated and the polymeric carrier is washed with DMF.

Example 2c

Coupling of a Hydrophobic Moiety to a Peptide Using Solid Phase Chemistry 910 mg of the polystyrene carrier loaded with a synthetic peptide of the SEQ ID NO:1 in which Tyr residue is protected with t-Bu group and Lys residues are protected with Boc groups obtained according to Example 1 are suspended with dichloromethane in a peptide reactor and kept for 30 minutes. The polystyrene carrier is then washed with DMF and afterwards suspended again in some DMF. In a separate jar 105 mg phenyl acetic acid, 239 mg TBTU and 103 mg HOBt are dissolved in DMF. Following the addition of 261 µl DIPEA and thorough stirring this solution is added to the suspended polystyrene carrier and the whole is flushed with nitrogen for about one hour. After the completeness of the conversion has been confirmed by a Kaiser test, the polymeric carrier is washed.

Example 2d

Coupling of a Hydrophobic Moiety to a Peptide Using Solid Phase Chemistry 910 mg of the polystyrene carrier loaded with a synthetic peptide of the SEQ ID NO:1 in which Tyr residue is protected with t-Bu group and Lys residues are protected with Boc groups obtained according to Example 1 are suspended with dichloromethane in a peptide reactor and kept for 30 minutes. The polystyrene carrier is then washed with DMF and afterwards suspended again in some DMF. In a separate jar 141 mg naphthyl acetic acid, 239 mg TBTU and 103 mg HOBt are dissolved in DMF. Following the addition of 261 µl DIPEA and thorough stirring this solution is added to the suspended polystyrene carrier and the whole is flushed with nitrogen for about one hour. After the completeness of the conversion has been confirmed by a Kaiser test, the polymeric carrier is washed.

Example 3a

Cleavage of a the Fully Protected Peptide from the Polymeric Carrier

From the polymeric carrier obtained according to Example 2a, the fully protected peptide is separated. To this end 20 ml of a solution comprising 1% by weight of trifluoroacetic acid in dichloromethane are added to the polymeric carrier material and the whole is shaken for about 2 minutes. The shaking process with the trifluoroacetic acid/dichloromethane solution is repeated seven times. Afterwards, the polymeric carrier is washed three times with dichloromethane and methanol. The combined cleavage and washing solutions are added to a solution of 10% by weight of pyridine in methanol, and the whole is then concentrated in vacuum to a volume corresponding to about 5% of the original volume. To the resulting solution are added about 80 ml pure water and the resulting white precipitate is filtrated. Following the repeated washing with cold water, cold $NaHCO_3$-solution, again cold water, cold 0.05M $KHSO_4$-solution and finally once again with water the precipitate obtained is dried with $P_2O_5$ in vacuum overnight. Yield 1.56 g of raw protected peptide.

Example 3b

Cleavage of the Deprotected Peptide from the Polymeric Carrier

The peptides as prepared according to Examples 2b, 2c and 2d are separated from the polymeric carrier while removing the protective groups of the side chains at the same time. To this end each 20 ml of a solution comprising 2.5% by weight of water, 2.5% by weight of tri-isopropyl silan and 95% by weight of trifluoroacetic acid are added to the polymeric carrier comprising the respective protected peptide and the whole mixture is then kept for about one hour. The polymeric carrier is then filtrated off and is afterwards washed twice with trifluoroacetic acid. Following the combination of the filtrate and the washing solutions the solvent is removed in vacuum. Crystallization of the resulting oily residue is initiated by a treatment in diethyl ether. Yield (raw unprotected peptide, in each case beige-colored crystals):

caprinoyl-peptide in which the peptide has the SEQ ID NO 1: 432 mg;

phenac-peptide in which the peptide has the SEQ ID NO 1: 370 mg;

naphtac-peptide in which the peptide has the SEQ ID NO 1: 395 mg.

Example 4

Coupling of palmitoyl-peptide in which the peptide has the SEQ ID NO 1 in which Tyr residues are protected with t-Bu group and Lys residues are protected with Boc groups to taurin (2-sulfoethyl-amine)

780 mg of the peptide obtained according to Example 3a are dissolved in 40 ml DMF. 160 mg TBTU, 68 mg HOBt, 340 µl N-ethyl-diisopropylamin and 125 mg taurin are added to this solution and the reaction mixture is stirred overnight in a nitrogen atmosphere; thereby the initial suspension turns into a clear solution. Finally, the solvent is removed in vacuum, and the solid residue is crystallized and washed with diethyl ether (yield: 1.4 g of a light brown solid).

The raw product, peptide in which the peptide has the SEQ ID NO in which Tyr residue is protected with t-Bu group and Lys residues are protected with Boc groups product is dissolved in 80 ml of a solution comprising 25% by weight of trifluoroacetic acid and 75 by weight of dichloromethane, and the whole mixture is stirred for about 90 minutes at room temperature. The solvent is then removed in vacuum and the remaining oily product is crystallized and washed with diethyl ether.

Example 5

The raw products as obtained in Examples 3b and 4 are purified by preparative HPLC(HPLC from Varian, reversed phase column with water/acetonitrile gradient and trifluoroacetic acid as modifier.

Yields and characterization:

(i) caprinoyl-peptide in which the peptide has the SEQ ID NO 1: 321 mg, ESI-MS: 955,6 [M+Na]$^+$

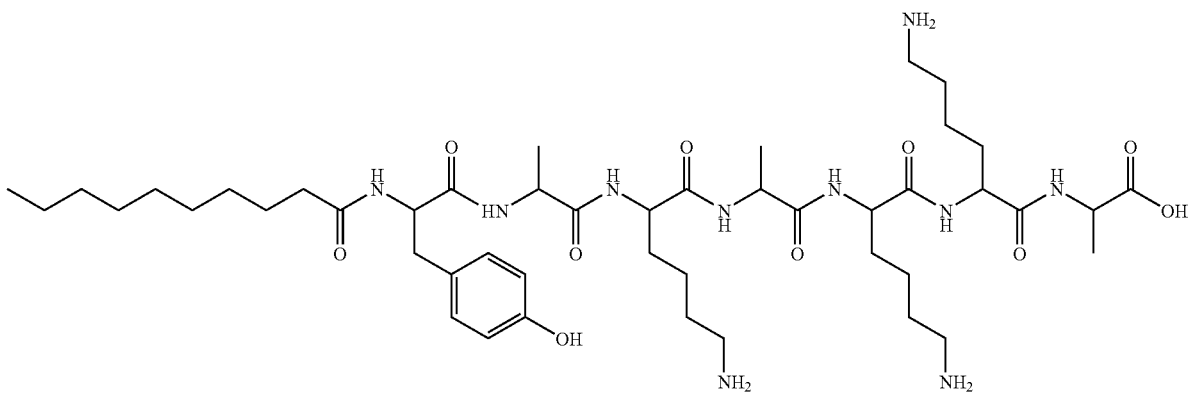

(ii) phenac-peptide in which the peptide has the SEQ ID NO 1: 276 mg, ESI-MS: 919,5 [M+Na]$^+$

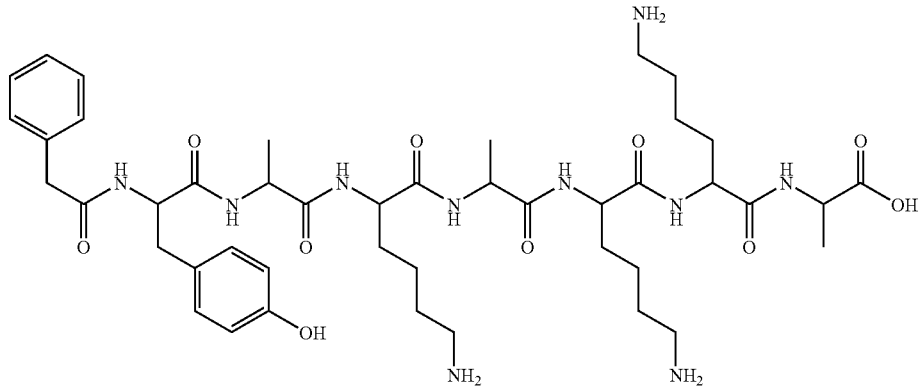

(iii) naphtac-peptide in which the peptide has the SEQ ID NO 1: 260 mg, ESI-MS: 969,5 [M+Na]$^+$

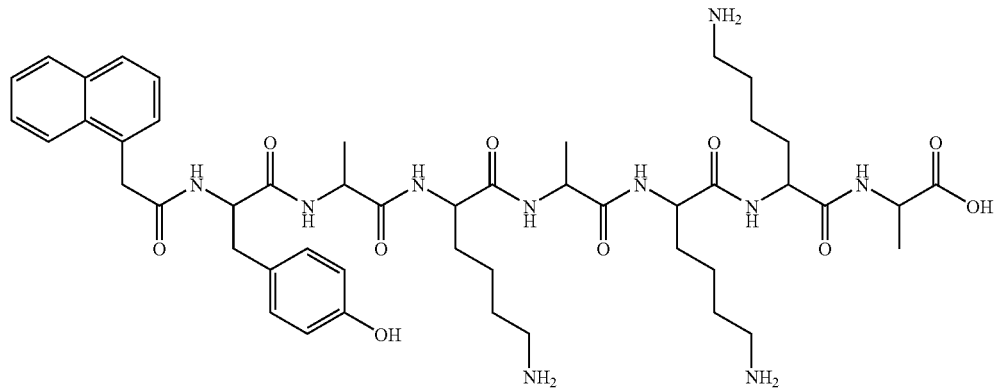

(iv) palmitoyl-peptide taurin in which the peptide has the SEQ ID NO 1: 406 mg, ESI-MS: 1146,7 [M+Na]+

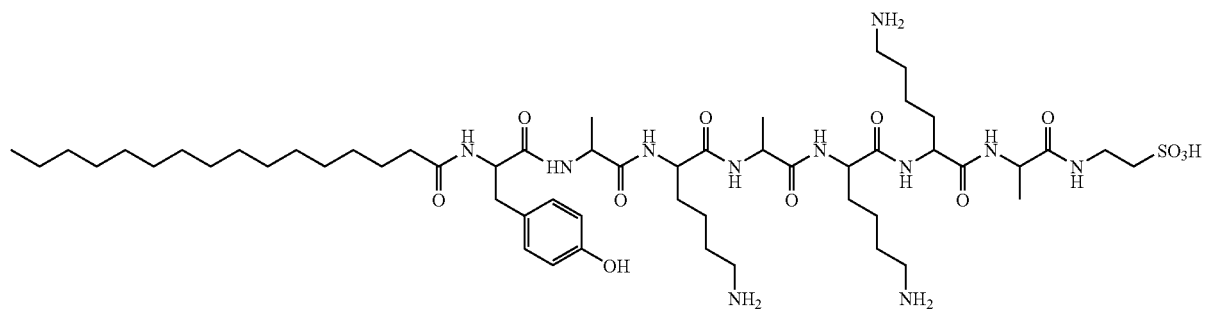

Example 6

Preparation of a Soft Silicon Hydrogel Contact Lens Having Attached to its Surface a Peptide which is Enzymatically Crosslinked A hydrophobic silicon hydrogel contact lens (lotrafilcon A, copolymerization product of a mixed polysiloxane/perfluoroalkyl polyether crosslinker, TRIS and DMA) is first incubated in an aqueous solution comprising 10 mmol of the purified peptide of Example 4 (palmitoyl-peptide-taurin in which the peptide has the SEQ ID NO 1) and is then transferred to an aqueous solution comprising 1% by weight of a casein hydrolysate (Vitalarmor). Enzymatical crosslinking is initiated by the addition of 2 U/ml of bacterial transglutaminase at 40° C. The coated lens is then washed with PBS buffer and autoclaved for 20 minutes at 121° C.

Example 7

Preparation of a Soft Silicon Hydrogel Contact Lens Having Attached to its Surface a Peptide which is Chemically Crosslinked (i) Preparation of the Silicon Hydrogel Contact Lens (ia) Preparation of PDMS Crosslinker I In a 4-L beaker, 24.13 g of $Na_2CO_3$, 80 g of NaCl and 1.52 kg of deionized water are mixed to dissolve. In a separate 4-L beaker, 700 g of bis-3-aminopropyl-polydimethylsiloxane (Shin-Etsu, MW ca. 11500) are dissolved in 1000 g of hexane. A 4-L reactor is equipped with overhead stirring with turbine agitator and a 250-mL addition funnel with micro-flow controller. The two solutions are then charged to the reactor, and mixed for 15 minutes with heavy agitation to produce an emulsion. 14.5 g of acryloyl chloride are dissolved in 100 mL of hexane and charged to the addition funnel. The acryloyl chloride solution is added dropwise to the emulsion under heavy agitation over one hour. The emulsion is stirred for 30 minutes on completion of the addition and then agitation is stopped and the phases are allowed to separate overnight. The aqueous phase is decanted and the organic phase is washed twice with a mixture of 2.0 kg of 2.5% NaCl dissolved in water. The organic phase is then dried over magnesium sulfate, filtered to 1.0 μm exclusion, and concentrated on a rotary evaporator. The resulting oil is further purified by high-vacuum drying to constant weight. Analysis of the resulting product by titration reveals 0.175 mEq/g of C═C double bonds.

(ib) Preparation of PDMS Crosslinker II

In a 4-L beaker, 61.73 g of $Na_2CO_3$, 80 g of NaCl and 1.52 kg of deionized water are mixed to dissolve. In a separate 4-L beaker, 700 g of bis-3-aminopropyl-polydimethylsiloaxane (Shin-Etsu, MW ca. 4500) are dissolved in 1000 g of hexane. A 4-L reactor is equipped with overhead stirring with turbine agitator and a 250-mL addition funnel with micro-flow controller. The two solutions are then charged to the reactor, and mixed for 15 minutes with heavy agitation to produce an emulsion. 36.6 g of acryloyl chloride is dissolved in 100 mL of hexane and charged to the addition funnel. The acryloyl chloride solution is added dropwise to the emulsion under heavy agitation over one hour. The emulsion is stirred for 30 minutes on completion of the addition and then agitation is stopped and the phases are allowed to separate overnight. The aqueous phase is decanted and the organic phase is washed twice with a mixture of 2.0 kg of 2.5% NaCl dissolved in water. The organic phase is then dried over magnesium sulfate, filtered to 1.0 µm exclusion, and concentrated on a rotary evaporator. The resulting oil is further purified by high-vacuum drying to constant weight. Analysis of the resulting product by titration reveals 0.435 mEq/g of C=C double bonds.

(ic) Preparation of the Crosslinkable Copolymer

A 2-L jacketed reactor is equipped with a heating/chilling loop, reflux condenser, $N_2$-inlet/vacuum adapter, feeding tube adapter and overhead mechanical stirring. A solution is generated by dissolving 90.00 g of PDMS crosslinker I according to (ia) and 30.00 g of PDMS crosslinker II according to (ib) in 480 g of 1-propanol. This solution is charged to the reactor and cooled to 8° C. The solution is degassed by evacuating to less than 15 mBar, holding at vacuum for 15 minutes, and then re-pressurizing with dry nitrogen. This degas procedure is repeated for a total of 3 times. The reactor is held under a blanket of dry nitrogen.

In a separate flask, a monomer solution is prepared by mixing 1.50 g of cysteamine hydrochloride, 0.3 g of AIBN, 55.275 g of DMA, 18.43 g of HEA and 364.5 g of 1-propanol. This solution is filtered with a Whatman 540 filter paper, and then added to the reactor through a degas unit and HPLC pump with a flow rate of 3.0 mL/minute. The reaction temperature is then elevated to 68° C. with a heating ramp about one hour.

In a second flask, a feeding solution is prepared by mixing 4.5 g of cysteamine hydrochloride and 395.5 g of 1-propanol and then filtering with Whatman 540 filter paper. When the reactor temperature reaches 68° C., this solution is slowly dosed into the reactor through the degasser/HPLC pump over 3 hours. The reaction is then continued at 68° C. for an additional 3 hours, on which heating has discontinued and the reactor is allowed to cool to room temperature.

The reaction mixture is transferred to a flask and stripped solvent at 40° C. under vacuum on a rotary evaporator until 1000 g of sample remained. The solution is then slowly mixed with 2000 g of deionized water with rapid agitation. Additional solvent is further removed until about 2000 g of sample remain. During this stripping process, the solution gradually becomes an emulsion. The resulting material is purified by ultrafiltration over a 10 kD molecular weight cut-off membrane until the permeate conductance is below 2.5 µS/cm. This emulsion is then charged to a 2-L reactor equipped with overhead stirring, refrigeration loop, thermometer, and the pH meter and dispensing tip of a Metrohm Model 718 STAT Titrino. The reaction mixture is then cooled to 1° C. 7.99 g of $NaHCO_3$ are charged to the emulsion and stirred to dissolve. The Titrino is set to maintain pH at 9.5 by intermittent addition of 15% sodium hydroxide solution. 11.59 mL of acryloyl chloride are then added over one hour using a syringe pump. The emulsion is stirred for another hour, then the Titrino is set to neutralize the reaction mixture by addition of a 15% solution of hydrochloric acid. The product is purified by ultrafiltration again with 10 kD molecular weight cut-off membrane until the permeate conductance is below 2.5 µS/cm. The final macromonomer is isolated by lypophilization.

(id) Preparation of Contact Lenses 18.83 g of the polymer obtained according to step (ic) are dissolved in approximately 200 mL of 1-propanol, concentrated to ca. 70 g total solution weight, and filtered to 0.45 µm exclusion. 67.94 g of solution at 26.53% solids are recovered. 4.503 g of a 1% solution of 2-hydroxy-4'-hydroxyethyl-2-methylpropiophenone (IRGACURE®-2959, Ciba Specialty Chemicals) are added, and then the solution is concentrated to a final weight of 25.74 g (65.0% solids).

200 mg of the formulation are dosed into poly(propylene) contact lens molds and the molds are closed. The molds are then irradiated for 15 s with an ultraviolet light source having an intensity of 2.18 mW/cm². The molds are then opened, and the mold halves which have a lens attached are soaked in a mixture of 80% isopropanol, 20% water (v/v) overnight. The lenses are rinsed off the molds with this solvent mixture, then rinsed twice for 2 hrs. each in fresh aliquots of isopropanol/water mixture. The lenses are drained and then hydrated by immersion in deionized water. They are then rinsed three times for 2 h in pure water (3.0 mL/lens).

(ie) Preparation of the Surface Coating

The hydrophobic silicon hydrogel contact lens obtained according to (id) above is incubated in isopropanol for 1 minute at 75° C. and is then transferred into a phosphate buffered saline solution comprising 10 mmol of the purified peptide of Example 4 (palmitoyl-Tyr-Ala-Lys-Ala-Lys-Lys-Ala-taurin) and treated for about 1 minute at 80° C. The contact lens is then transferred into buffered saline and 100 µl of a 2% by weight formaldehyde solution are added. The contact lens is afterwards autoclaved for 30 minutes at 121° C. The attachment of the peptide of Example 4 can be monitored by nitration reaction of the thyrosine moiety in the peptide chain with tetranitro-methane leading to a yellow staining. The hydrophilic surface coating is investigated by visual wettability and hydrophilicity testing as well as contact angle measurements and the Sudan Black staining test.

(if) Water Contact Angle Measurement

The measurement is performed by the sessile drop method with a DSA 10 drop shape analysis system from Krüss GmbH, Germany with pure water (Fluka, surface tension 72.5 mN/M at 20° C.). For measurement purposes a contact lens is taken off the storage solution with tweezers and excess storage solution is removed by gentle shaking. The contact lens is placed on the male part of a contact lens mold and gently blotted with a dry and clean cloth. A water droplet (about 1 µl) is then dosed on the lens apex, and the change of the contact angle over time of this water droplet (WCA(t), circle fitting mode) is monitored; WCA is calculated by extrapolation of the graph WCA(t) to t=0.

(ig) Sudan Black Dye Absorption Test

A 0.5% (w/w) Sudan Black dye solution is prepared by dissolving 0.5 g of Sudan Black B (Aldrich) over night in 100 g of vitamin E oil under stirring. For measurement purposes, the surface-treated lens is first of all autoclaved (30 min, 121° C.) in 2 ml of an phosphate buffered saline (pH 7.2) in a glass vial. The contact lens is then removed from the solution with tweezers and gently shaken so that most of the surface water is removed. The lens is then placed in the above prepared Sudan Black dye solution for 5 min. Thereafter the lens is removed from the dye-bath, and the excess dye solution is rinsed off with warm water. The lens is air-dried and assessed according to its degree of staining.

2=no or almost no staining
1=slight staining
0=considerable staining (ih) The Values Obtained with Contact Lenses as Coated According to (ie) and with the Corresponding Uncoated Contact Lenses (Control) are Summarized in Table I

| Example | WCA [°] | Sudan Black |
|---|---|---|
| ie | 58 | 2 |
| (Control) | 109 | 0 |

The invention claimed is:

1. A process for the manufacture of a composite material, comprising the steps of:
   (a) providing a hydrophobic organic bulk material;
   (b) applying a hydrophilic surface coating on the hydrophobic organic bulk material by first non-covalently attaching to the surface of the bulk material a water-soluble peptide comprising a hydrophobic moiety, wherein the water-soluble peptide is of the formula A-C(O)-[NH-(peptide)-C(O)]-X$_1$-R$_3$     (3), wherein A-C(O) is a radical selected from the group consisting of the radical of a fatty acid, the radical of an aromatic carboxylic acid and the radical of an araliphatic carboxylic acid, [NH-(peptide)-C(O)] is the radical of a polypeptide which is a statistical copolymer of lysine and more than one other amino acids selected from the group consisting of alanine, phenylalanine, serine, tyrosine and tryptophan, and wherein the molecular weight range M$_r$ of the polypeptide is from 400 to 10000 daltons,
   X$_1$—R$_3$ is either OH and part of the terminal peptide carboxy group, or X$_1$ is O or NR$_4$ wherein R$_4$ is hydrogen or C$_1$—C$_2$-alkyl, and R$_3$ is a hydrophilic group; and
   (c) then chemically or enzymatically crosslinking said water-soluble peptide.

2. The process according to claim 1, wherein the hydrophobic organic bulk material is a polysiloxane, perfluoroalkyl polyether, fluorinated poly(meth)acrylate, polyalkyl (meth) acrylate, fluorinated polyolefin or a mixture thereof.

3. The process according to claim 1, wherein the hydrophobic organic bulk material is a polysiloxane hydrogel, a perfluoroalkyl polyether hydrogel or a mixture thereof.

4. The process according to claim 1, wherein the polypeptide underlying the polypeptide radical [NH-(peptide)-C(O)] is the radical of a polypeptide having from 3 to 20 amino acid residues and having a statistical composition consisting of one tyrosine residue, 1 to 8 alanine residues, and 1 to 20 lysine residues.

5. The process according to claim 4, wherein the polypeptide underlying the polypeptide radical [NH-(peptide)-C(O)] is a statistical copolymer consisting of one tyrosine (Tyr) residue, 3 alanine (Ala) residue, and 3 lysine (Lys) residues.

6. The process according to claim 4, wherein the hydrophilic surface coating is finalized by chemically initiating the crosslinking of the water soluble peptide being attached to the organic bulk material with a crosslinking agent selected from formaldehyde or glutaraldehyde.

7. The process according to claim 4, wherein the hydrophilic surface coating is finalized by enzymatic crosslinking of the water soluble peptide being attached to the organic bulk material with a peptide substrate of transglutaminase.

8. The process according to claim 1, wherein the polypeptide underlying the polypeptide radical [NH-(peptide)-C(O)] is a copolymer of the SEQ ID NO 1:

Tyr-Ala-Lys-Ala-Lys-Lys-Ala     (4c), wherein Tyr is linked to A, and Ala is linked to R$_3$.

9. The process according to claim 1, wherein the hydrophilic surface coating is finalized by chemically initiating the crosslinking of the water soluble peptide being attached to the organic bulk material with a crosslinking agent selected from formaldehyde or glutaraldehyde.

10. The process according to claim 1, wherein the hydrophilic surface coating is finalized by enzymatic crosslinking of the water soluble peptide being attached to the organic bulk material with a peptide substrate of transglutaminase.

11. The process according to claim 10,
    wherein the peptide substrate is a peptide that contains glutamine.

12. The process according to claim 11, wherein the composite material is a contact lens.

13. The process according to claim 12, wherein the polypeptide underlying the polypeptide radical [NH-(peptide)-C(O)] is a copolymer of the SEQ ID NO 1:

Tyr-Ala-Lys-Ala-Lys-Lys-Ala     (4c), wherein Tyr is linked to A, and Ala is linked to R$_3$.

14. The process according to claim 1, wherein the polypeptide underlying the polypeptide radical [NH-(peptide)-C(O)] is a statistical copolymer of lysine and an amino acid selected from the group consisting of alanine, and tyrosine.

* * * * *

```
                         SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: synthetic

<400> SEQUENCE: 1

Tyr Ala Lys Ala Lys Lys Ala
1               5
```